United States Patent
Tanaka et al.

(10) Patent No.: US 9,900,521 B2
(45) Date of Patent: Feb. 20, 2018

(54) IMAGING DEVICE HAVING AN EXPOSURE TIME CALCULATION FUNCTION AND IMAGING METHOD

(71) Applicant: FUJIFILM Corporation, Tokyo (JP)

(72) Inventors: Yasutake Tanaka, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/042,448

(22) Filed: Feb. 12, 2016

(65) Prior Publication Data
US 2016/0255263 A1    Sep. 1, 2016

(30) Foreign Application Priority Data

Feb. 27, 2015    (JP) ................................ 2015-038295

(51) Int. Cl.
*H04N 5/235*    (2006.01)
*H04N 5/232*    (2006.01)
(Continued)

(52) U.S. Cl.
CPC ....... *H04N 5/2356* (2013.01); *G01N 21/6456* (2013.01); *G03B 7/093* (2013.01);
(Continued)

(58) Field of Classification Search
CPC .. H04N 5/2356; H04N 5/2353; H04N 5/2354; H04N 5/23293; H04N 5/347;
(Continued)

(56) References Cited

U.S. PATENT DOCUMENTS 4,471,228 A * 9/1984 Nishizawa ........ H01L 27/14679
                                                250/208.1
4,475,802 A 10/1984 Onogi
(Continued)

FOREIGN PATENT DOCUMENTS

GB    2409288 A    6/2005
JP    2014-39116 A    2/2014

OTHER PUBLICATIONS

Extended European Search Report, dated Jun. 30, 2016, for European Application No. 16153328.6.
European Office Action, dated Jul. 19, 2017, for European Application No. 16153328.6.

*Primary Examiner* — Albert Cutler
(74) *Attorney, Agent, or Firm* — Birch, Stewart, Kolasch & Birch, LLP

(57) ABSTRACT

Disclosed is a imaging device and method capable of quickly informing a user of failure of sample creation and preventing useless imaging from being performed. The imaging device includes an imaging unit which images an object, an exposure time calculation unit which calculates, based on an image signal acquired by imaging of the imaging unit, an exposure time of the imaging until a signal value of the image signal reaches a target signal value set in advance, a determination unit which determines whether or not the exposure time exceeds a threshold value set in advance, and a display control unit which, in a case where it is determined that the exposure time exceeds the threshold value set in advance, gives notification of the result of the determination.

15 Claims, 7 Drawing Sheets

(51) Int. Cl.
*G01N 21/64* (2006.01)
*H04N 5/347* (2011.01)
*G03B 17/18* (2006.01)
*G03B 7/093* (2006.01)

(52) U.S. Cl.
CPC ........... *G03B 17/18* (2013.01); *H04N 5/2351* (2013.01); *H04N 5/2353* (2013.01); *H04N 5/2354* (2013.01); *H04N 5/23293* (2013.01); *H04N 5/347* (2013.01)

(58) Field of Classification Search
CPC ...... H04N 5/2351; H04N 5/235; H04N 5/351; H04N 5/353; G01N 21/6456; G01N 21/6458; G03B 7/093; G03B 17/18; G03B 7/00
See application file for complete search history.

(56) References Cited

U.S. PATENT DOCUMENTS

| | | | |
|---|---|---|---|
| 5,585,942 A | 12/1996 | Kondo | |
| 5,682,567 A | 10/1997 | Spruck et al. | |
| 6,693,673 B1 * | 2/2004 | Tanaka | H04N 5/2352 348/223.1 |
| 6,791,618 B1 * | 9/2004 | Shimizu | H04N 5/2351 348/362 |
| 2007/0009245 A1 * | 1/2007 | Ito | G03B 17/02 396/55 |
| 2013/0146750 A1 * | 6/2013 | Maeda | H01L 27/14601 250/208.1 |
| 2013/0243283 A1 * | 9/2013 | Kotchou | G06T 7/0012 382/128 |

\* cited by examiner

IMAGING DEVICE HAVING AN EXPOSURE TIME CALCULATION FUNCTION AND IMAGING METHOD

CROSS-REFERENCE TO RELATED APPLICATIONS

The present application claims priority under 35 U.S.C. § 119 to Japanese Patent Application No. 2015-038295, filed on Feb. 27, 2015. Each of the above application(s) is hereby expressly incorporated by reference, in its entirety, into the present application.

BACKGROUND OF THE INVENTION

1. Field of the Invention

The present invention relates to an imaging device and method which images light emitted from an object with an imaging element.

2. Description of the Related Art

Hitherto, an imaging system which arranges an object in a housing and irradiates an object with light using a light source in the housing to image the object has been used in various fields.

Among such imaging systems, an imaging system which selectively uses an imaging method according to the type of object, and images, for example, chemiluminescence, fluorescence, or reflected light from the object, or transmitted light transmitted through the object with an imaging element to generate an image has been suggested.

SUMMARY OF THE INVENTION

For example, in a case where a result of electrophoresis of fluorescence-labeled protein on a gel support is imaged with the above-described imaging system, while an operation to transfer fluorescence-labeled protein on the gel support to a membrane is performed, the transfer may not be appropriately performed and sample creation may fail.

In general, since fluorescence emitted from a fluorescent label is weak, in a case where an image of fluorescence is imaged, a comparatively long exposure time is required until a target signal value is obtained; however, as described above, if imaging is performed over a long exposure time even when sample creation fails, the user wastes time, the use of the imaging system of other users is uselessly inhibited, and the use efficiency of the imaging system is degraded.

JP2014-39116A has suggested that, for imaging an object using an imaging element, a remaining exposure time until appropriate exposure is completed is calculated, and the remaining exposure time is displayed and informed to the user; however, there is no suggestion of a method which prevents useless imaging due to failure of sample creation described above.

An object of the invention is to provide an imaging device and method capable of quickly informing a user of failure of sample creation described above and preventing useless imaging from being performed, in consideration of the problems described above.

An imaging device of the invention includes an imaging unit which images an object, an exposure time calculation unit which calculates, based on an image signal acquired by imaging of the imaging unit, an exposure time of the imaging until a signal value of the image signal reaches a target signal value set in advance, a determination unit which determines whether or not the exposure time exceeds a threshold value set in advance, and a notification unit which, in a case where it is determined that the exposure time exceeds the threshold value, gives notification of the result of the determination.

In the imaging device of the invention, the imaging unit may have an imaging element which is able to read the image signal nondestructively, and the exposure time calculation unit may calculate the exposure time based on the image signal read nondestructively.

In the imaging device of the invention, the exposure time calculation unit may acquire image signal read multiple times nondestructively and continuously and may calculate the exposure time based on the image signals acquired by reading multiple times.

In the imaging device of the invention, the exposure time calculation unit may sequentially calculate the exposure time each time the image signal read nondestructively is acquired.

The imaging device of the invention may further include a display control unit which makes a display unit sequentially display images based on the image signals read nondestructively and continuously.

In the imaging device of the invention, the imaging unit may perform pre-imaging before main imaging, and the exposure time calculation unit may calculate the exposure time based on an image signal acquired by the pre-imaging.

In the imaging device of the invention, the determination unit may change the threshold value between in a case where chemiluminescence of the object is imaged and in a case where fluorescence of the object is imaged.

In the imaging device of the invention, the exposure time calculation unit may change a calculation expression for use in calculating the exposure time between in a case where chemiluminescence of the object is imaged and in a case where fluorescence of the object is imaged.

In the imaging device of the invention, the imaging unit may stop the imaging in a case where it is determined that the exposure time exceeds the threshold value.

In the imaging device of the invention, the exposure time calculation unit may acquire an image signal read with binning by the imaging unit and may calculate the exposure time based on the acquired image signal.

The notification unit may perform a warning in a case where it is determined that the exposure time exceeds the threshold value.

The notification unit may make a display unit display a warning message in a case where it is determined that the exposure time exceeds the threshold value.

An imaging method of the invention using the imaging device includes imaging an object to acquire an image signal, calculating, based on the acquire image signal, an exposure time of the imaging until a signal value of the image signal reaches a target signal value set in advance, determining whether or not the exposure time exceeds a threshold value set in advance, and in a case where it is determined that the exposure time exceeds the threshold value, giving notification of the result of the determination.

According to the imaging device and method of the invention, the object is imaged to acquire the image signal, the exposure time of imaging until the signal value of the image signal reaches the target signal value set in advance is calculated based on the acquire image signal, and it is determined whether or not the calculated exposure time exceeds the threshold value set in advance. Then, in a case where it is determined that the exposure time exceeds the threshold value, it is estimated that creation of a sample as the object fails and the amount of light emitted from the sample is excessively small, and the result of the determination is notified to the user. With this, it is possible to quickly inform the user of failure of sample creation and to prevent useless imaging from being performed.

DESCRIPTION OF THE PREFERRED EMBODIMENTS

Figure 1:
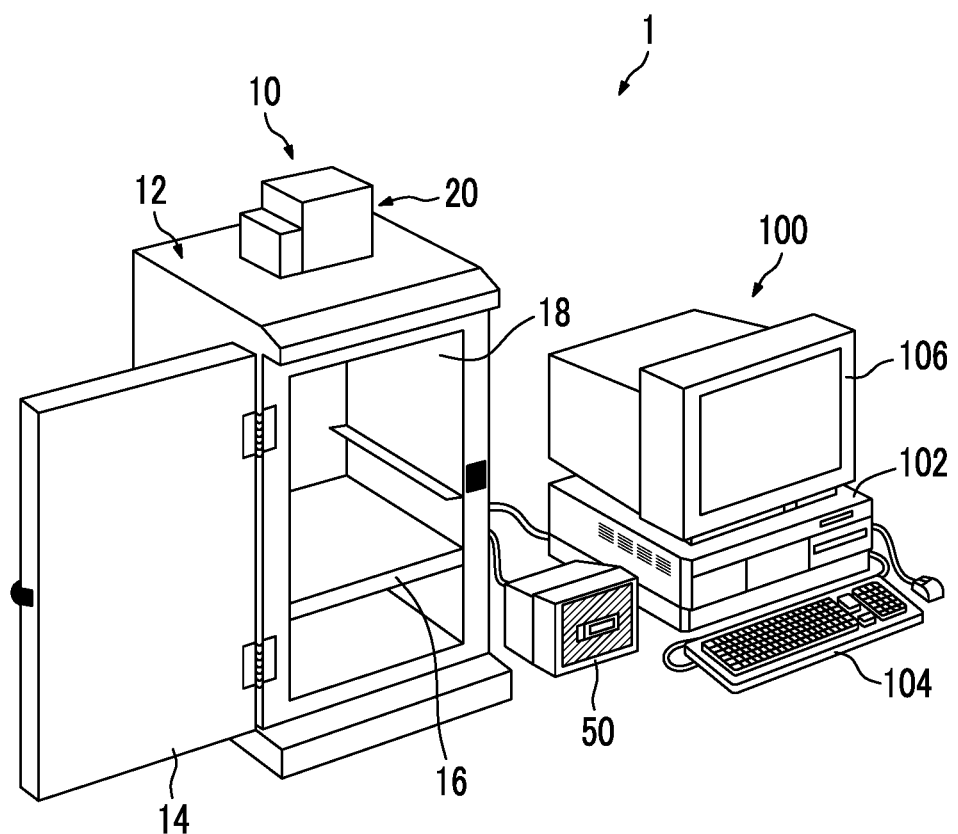
FIG. 1 is a schematic perspective view of an imaging system using an embodiment of an imaging device of the invention.

Hereinafter, an imaging system 1 using a first embodiment of an imaging device and method of the invention will be described in detail referring to the drawings. FIG. 1 is a schematic perspective view showing an imaging system of this embodiment, FIG. 2 is a schematic sectional view showing the internal configuration of an imaging device of this embodiment, and FIG. 3 is a schematic block diagram showing the imaging system of the embodiment.

Figure 2:
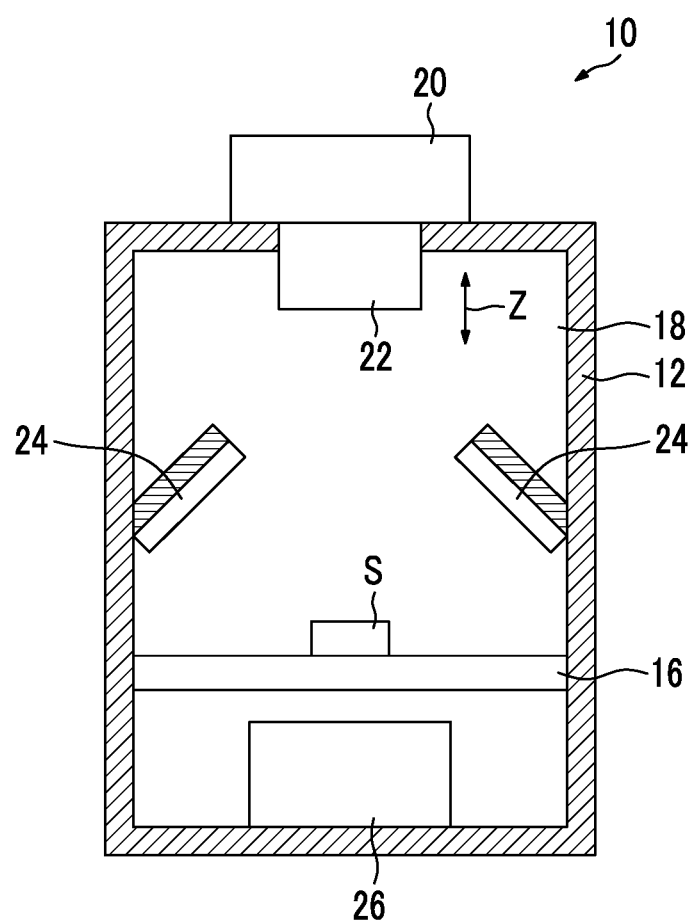
FIG. 2 is a schematic sectional view showing the internal configuration of an embodiment of an imaging device of the invention.
Figure 3:
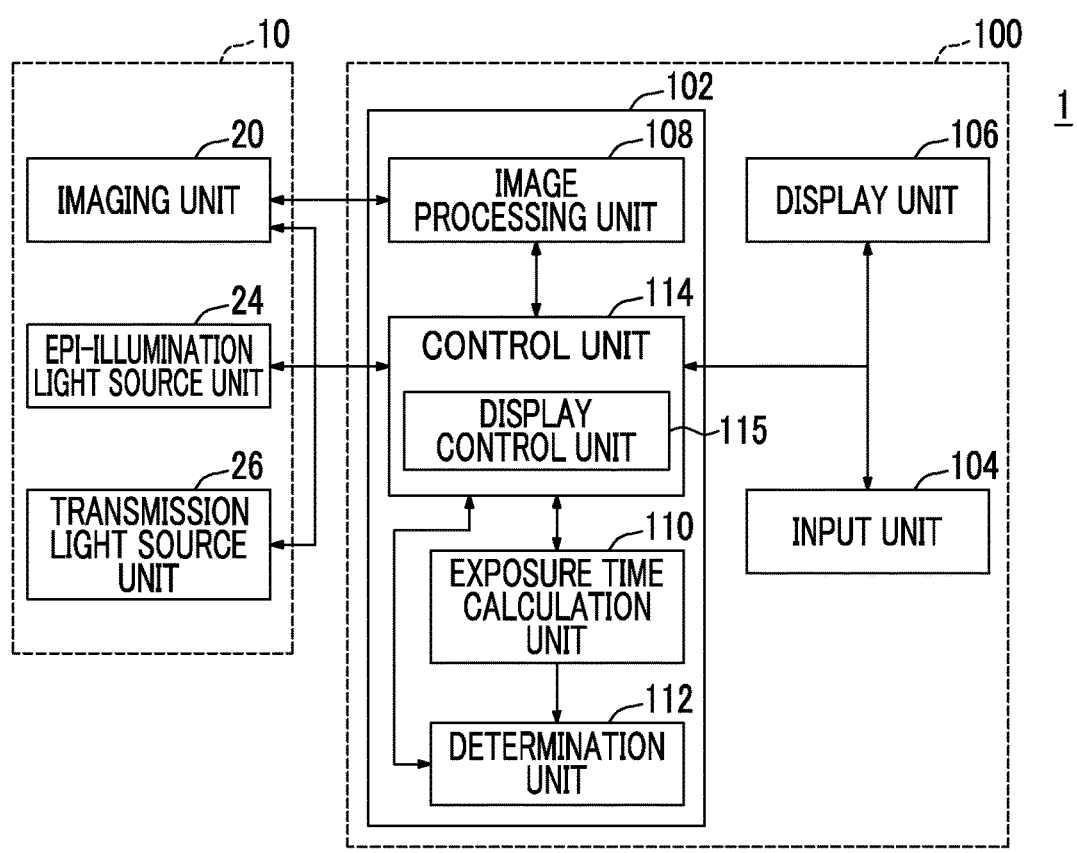
FIG. 3 is a schematic block diagram of an embodiment of an imaging device of the invention.

As shown in FIGS. 1 and 2, the imaging system 1 of this embodiment includes a black box 10 and an imaging control device 100.

The black box 10 includes a housing 12 having a door 14, a stage 16 on which an object S is placed, an imaging unit 20, a lens unit 22, an epi-illumination light source unit 24, a transmission light source unit 26, and an object observation monitor 50.

The housing 12 has a hollow portion 18 which is formed in a substantially rectangular parallelepiped, and is provided with the stage 16 on which the object S is arranged. The door 14 shown in FIG. 1 is openably and closably attached to the housing 12, and the user opens the door 14, arranges the object S on the stage 16, and closes the door 14, thereby accommodating the object S in the housing 12. The housing 12 constitutes a black box such that external light does not enter the hollow portion 18. The stage 16 is formed of a material which transmits light from the transmission light source unit 26.

The imaging unit 20 is fixed to the top surface of the housing 12, includes, for example, an imaging element, such as a cooled charge coupled device (CCD) image sensor or a complementary metal-oxide semiconductor (CMOS) image sensor, and detects light reflected from the object S, light emitted from the object S, or light transmitted through the object S to generate an image signal. The image signal generated in the imaging unit 20 is subjected to, for example, an amplification process and is then output to the imaging control device 100.

The imaging unit 20 is attached to the lens unit 22. The lens unit 22 includes, for example, a plurality of lenses, and is provided to be movable in an arrow Z direction in order to focus on the object S. The lens unit 22 also includes, for example, optical elements, such as a diaphragm and an excitation light cut filter, and adjusts the amount or wavelength of light to be detected.

The epi-illumination light source unit 24 and the transmission light source unit 26 respectively have, for example, an excitation light source for fluorescent imaging and a white light source, and is configured to switch between the light sources as necessary under the control of the imaging control device 100. For example, in case of performing imaging to detect fluorescence emitted from the fluorescence-labeled object S, the object S is irradiated with excitation light from the epi-illumination light source unit 24 or the transmission light source unit 26, in case of performing imaging to detect reflected light from the object S, the object S is irradiated with white light from the epi-illumination light source unit 24, and in case of performing imaging to detect transmitted light transmitted through the object S, the object S is irradiated with white light from the transmission light source unit 26.

The object observation monitor 50 displays a state on the stage 16 imaged with a small-sized camera (not shown) provided in the upper portion of the housing 12. With this, it is possible to confirm the position of the object S arranged on the stage 16 or the height of the stage 16, and to adjust the position of the object or the height of the stage such that the object S is arranged suitably for imaging.

The imaging control device 100 is constituted of, for example, a computer, and includes a control device body 102, an input unit 104, and a display unit 106. The imaging control device 100 controls the operation of the imaging unit 20, the epi-illumination light source unit 24, and the transmission light source unit 26 of the black box 10, and the black box 10 images the object S under the control of the imaging control device 100. In this embodiment, the imaging unit 20 in the black box 10, an exposure time calculation unit 110, a determination unit 112, and a display control unit 115 in the imaging control device 100 constitute an imaging device of the invention. In this embodiment, the display control unit 115 corresponds to a notification unit of the invention.

As shown in FIG. 3, the control device body 102 includes an image processing unit 108, an exposure time calculation unit 110, a determination unit 112, and a control unit 114.

The image processing unit 108 receives the image signal output from the imaging unit 20 as input, and subjects the image signal to necessary signal processes (for example, a noise elimination process, a sharpness process, or the like).

The exposure time calculation unit 110 calculates, based on the image signal output from the imaging unit 20, the exposure time of imaging until the signal value of the image signal reaches a target signal value set in advance. As the signal value of the image signal, a representative value, such as the average value of an image signal representing one image output from the imaging element, a k-th signal value (where k is a natural number) from a maximum, a k-th signal value from a minimum, or a median value, can be used. The target signal value is a value of an image signal that the user targets, and is set in advance. The target signal value may be arbitrarily set by the user using the input unit 104.

In this embodiment, a CMOS image sensor is used as the imaging element, and the exposure time is calculated based on an image signal read nondestructively from the imaging element after the start of imaging. Nondestructive reading is a method which, for reading an image signal from the imaging element, reads the image signal while maintaining the storage state without emptying an electric charge stored in each photoelectric conversion element constituting the imaging element. That is, since a reset process is not performed for reading the image signal, it is possible to read the image signal any number of times in the middle of storing an electric charge. The calculation method of the exposure time will be described below in detail.

The determination unit 112 compares the exposure time calculated in the exposure time calculation unit 110 with a threshold value set in advance and determines whether or not the exposure time exceeds the threshold value. If creation of a sample (object S) is successful, the threshold value is a sufficient period of time as an exposure time for acquiring an image signal of a desired size, and may be acquired in advance, for example, by an experiment or the like.

The control unit 114 includes, for example, a central processing unit (CPU), a read only memory (ROM), and the like. The control unit 114 integrally controls the respective units in the black box 10 and the operation of the imaging control device 100. The control unit 114 also includes the display control unit 115. The display control unit 115 makes the display unit 106 display an image for observation based on the image signal output from the imaging unit 20. Furthermore, in a case where the determination unit 112 determines that the exposure time calculated by the exposure time calculation unit 110 exceeds the threshold value, the display control unit 115 makes the display unit 106 display a warning, such as a message of informing the user to that effect. As a warning message, for example, there are a message to the effect that creation of a sample fails, a message to the effect that a sample is abnormal, and the like. The invention is not limited to the message, and an index, such as a mark, may be displayed. In this embodiment, although the message or the like is displayed to give a warning to the user, the invention is not limited thereto, and a lamp is turned on or sound is made to inform the user of failure of sample creation or an abnormal sample.

The display unit 106 includes, for example, a display device, such as a cathode ray tube (CRT) display or a liquid crystal display, and displays the image for observation or displays the warning message as described above. The display unit 106 also displays a setup screen for performing various settings in the respective units of the black box 10 or giving an instruction.

The input unit 104 includes a mouse, a keyboard, and the like. The user performs various settings in the respective units of the black box 10 or gives an instruction using the input unit 104. The user sets and inputs, for example, information regarding an imaging method and information regarding the name of a reagent to be used using the input unit 104. The set and input information is stored in, for example, a storage unit (not shown) in the control unit 114.

The imaging system 1 of this embodiment has the above-described configuration, and can perform imaging using four imaging methods according to the type of object or the purpose of imaging. As the four imaging methods, there are an imaging method (hereinafter, referred to as a first imaging method) which detects chemiluminescence emitted from the object, an imaging method (hereinafter, referred to as a second imaging method) which detects fluorescence emitted from the object, an imaging method (hereinafter, referred to as a third imaging method) which detects reflected light reflected from the object, and an imaging method (hereinafter, referred to as a fourth imaging method) which detects transmitted light transmitted from the object.

In the first imaging method, when an object molecule excited by a chemical reaction is returned to a ground state, a phenomenon (chemiluminescence) in which energy is discharged as light is used. With this, for example, it is possible to perform genetic analysis, inspection and research of a biological tissue relating to diseases or aging, deterioration evaluation of an organic compound and a high molecular compound, and the like. For example, an imaging target substance in the object is labeled with a label substance which causes chemiluminescence if coming into contact with a chemiluminescent substrate, and thereafter, the chemiluminescent substrate comes into contact with the label substance, whereby chemiluminescence can be generated. In the first imaging method, light irradiation from the epi-illumination light source unit 24 and the transmission light source unit 26 is not performed.

In the second imaging method, excitation light from the epi-illumination light source unit 24 or the transmission light source unit 26 is irradiated, and fluorescence is detected from a fluorescence substance which labels an imaging target substance in the object. As the object of the second imaging method, for example, a gel support including deoxyribonucleic acid (DNA) fragments fluorescent-labeled and separated by electrophoresis is considered. If this imaging system 1 is used, it is possible to image and evaluate the distribution of the DNA fragments in the gel support.

In the third imaging method, for example, white light is irradiated from the epi-illumination light source unit 24 as illumination light, and reflected light of illumination light from the object is detected. With this, it is possible to obtain a digital image by photoelectrically reading a reflective original, such as a photograph. In the fourth imaging method, for example, white light is irradiated from the transmission light source unit 26 as illumination light, and transmitted light of illumination light transmitted through the object is detected. With this, it is possible to obtain a digital image by photoelectrically reading a transmissive original, such as a film.

Next, the action of the imaging system 1 of this embodiment will be described referring to the flowchart shown in FIG. 4. While the imaging system 1 of this embodiment can perform imaging using the four imaging methods as described above, it is assumed that the first and second imaging methods are primarily executed, that is, chemiluminescence and fluorescence emitted from the object S are imaged.

First, after the object S is placed on the stage 16 of the black box 10, an imaging start instruction is input by the user using the input unit 104, and imaging by the imaging unit 20 is started. Specifically, the exposure of the imaging element of the imaging unit 20 is started.

Then, when a time t1 set in advance has elapsed from the start of imaging, the image signal is read from the imaging element of the imaging unit 20 by nondestructive reading, and the image signal is acquired by the exposure time calculation unit 110 (S12).

The exposure time calculation unit 110 calculates, based on the input image signal by nondestructive reading, the exposure time until the signal value of the image signal reaches the target signal value set in advance (S14).

Figure 5:
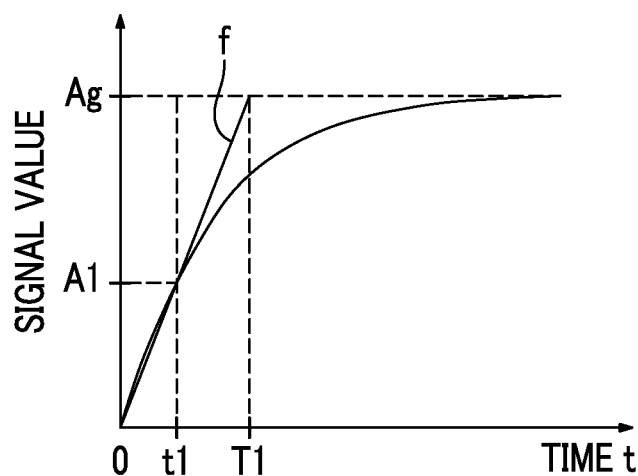
FIG. 5 is a diagram illustrating a calculation method of an exposure time.

Specifically, as shown in FIG. 5, a linear function f is determined using the time t1 set in advance and a signal value A1 of the image signal by nondestructive reading, and an exposure time T when the value of the linear function f reaches a target signal value Ag is calculated. In this case, the exposure time T can be calculated by $T=Ag/(A1/t1)$. A curve shown in FIG. 5 indicates a signal value of an image which is expected to be actually obtained for imaging chemiluminescence or fluorescence emitted from a sample appropriately created. The linear function approximates the curve.

For calculating the exposure time as described above, as the image signal by nondestructive reading, image signals read from all photoelectric conversion elements may not necessarily be used, and only image signals read some photoelectric conversion elements among the photoelectric conversion elements constituting the imaging element may be used.

The exposure time T calculated by the exposure time calculation unit 110 is input to the determination unit 112, and the determination unit 112 compares the input exposure time T with a threshold value Tth set in advance. At this time, instead of the threshold value determination of the exposure time T, threshold value determination of an exposure time obtained by subtracting the time t1 from the exposure time T, that is, a remaining exposure time, may be performed.

Then, in a case where the exposure time T exceeds the threshold value Tth (S16, YES), the determination unit 112 outputs a signal to that effect to the display control unit 115.

In a case where the signal to the effect that the exposure time T exceeds the threshold value Tth is input, as described above, the display control unit 115 makes the display unit 106 display the message to the effect that creation of a sample fails, the message to the effect that a sample is abnormal, or the like, and gives a warning to the user (S18).

In a case where the signal to the effect that the exposure time T exceeds the threshold value Tth is input, the control unit 114 automatically stops the imaging operation of the imaging unit 20 (S20).

In a case where the determination unit 112 determines that the exposure time T is equal to or less than the threshold value Tth (S16, NO), imaging by the imaging unit 20 is continued as it is (S22), and when the exposure time T has elapsed (S24), the image signal is read from the imaging element of the imaging unit 20 by destructive reading (S26). Destructive reading is a reading method in which, for reading the image signal from the photoelectric conversion element of the imaging element, a reset process for emptying an electric charge stored in the photoelectric conversion element is performed.

Then, the image signal acquired by destructive reading is input to the image processing unit 108, and is subjected to signal processes in the image processing unit 108. The image signal subjected to the signal processes is input to the display control unit 115, and the display control unit 115 makes the display unit 106 display the image for observation based on the image signal subjected to the signal processes (S28).

According to the imaging system of the foregoing embodiment, the exposure time until the signal value reaches the target signal value set in advance is calculated based on the image signal obtained by imaging the object, and it is determined whether or not the calculated exposure time exceeds the threshold value set in advance. Then, in a case where it is determined that the exposure time exceeds the threshold value, it is estimated that creation of a sample as the object fails and the amount of light emitted from the sample is excessively small, and the determination result is informed to the user. With this, it is possible to quickly inform the user of failure of sample creation, and to prevent useless imaging from being performed.

In the foregoing embodiment, although the exposure time T is calculated based on the image signal acquired by single nondestructive reading, the invention is not limited, and a plurality of image signals are acquired by performing nondestructive reading multiple times, and the exposure time T may be acquired based on a plurality of image signals.

Figure 6:
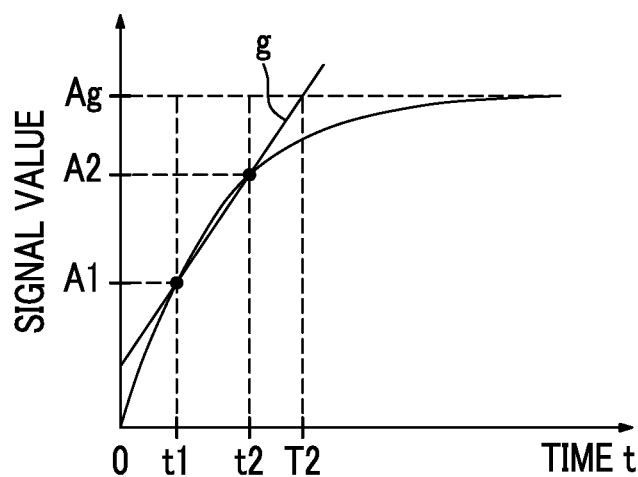
FIG. 6 is a diagram illustrating a method of calculating an exposure time based on image signals acquired by performing nondestructive reading multiple times.

Specifically, for example, as shown in FIG. 6, after nondestructive reading is performed at the time t1 set in advance to acquire a first image signal, nondestructive reading is performed at a time t2 set in advance to acquire a second image signal. Then, a linear function g may be determined using the time t1 and a signal value A1 of the first image signal, and the time t2 and a signal value A2 of the second image signal, and the exposure time T when the value of the linear function g reaches the target signal value Ag may be calculated. In this case, the exposure time T can be calculated by $T=Ag/\{(A2-A1)/(t2-t1)\}$. In this way, the linear function g is determined based on a plurality of image signals acquired by performing nondestructive reading multiple times, and can be approximated by a curve shown in FIG. 6, that is, the exposure time T can be calculated with higher accuracy. Similarly to the curve shown in FIG. 5, the curve shown in FIG. 6 indicates a value of an image signal which is expected to be actually obtained when imaging chemiluminescence or fluorescence emitted from a sample appropriately created.

Figure 7:
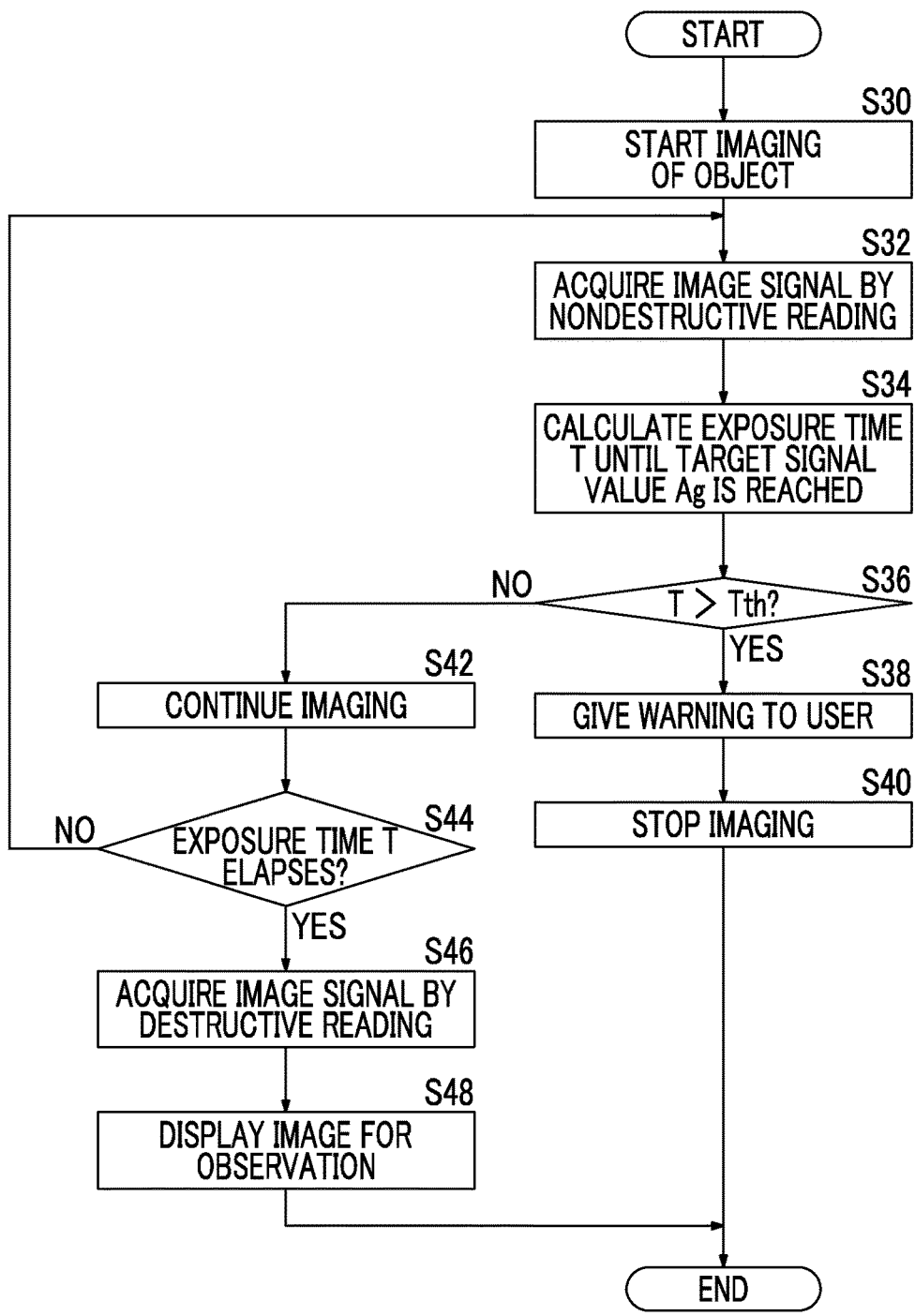
FIG. 7 is a flowchart illustrating a method of sequentially calculating an exposure time each time an image signal is acquired by performing nondestructive reading.

In a case where nondestructive reading is performed multiple times as described above, the exposure time T may be calculated each time the image signal is acquired by nondestructive reading, and the determination may be performed in the determination unit 112 each time. FIG. 7 is a flowchart in this case.

Figure 4:
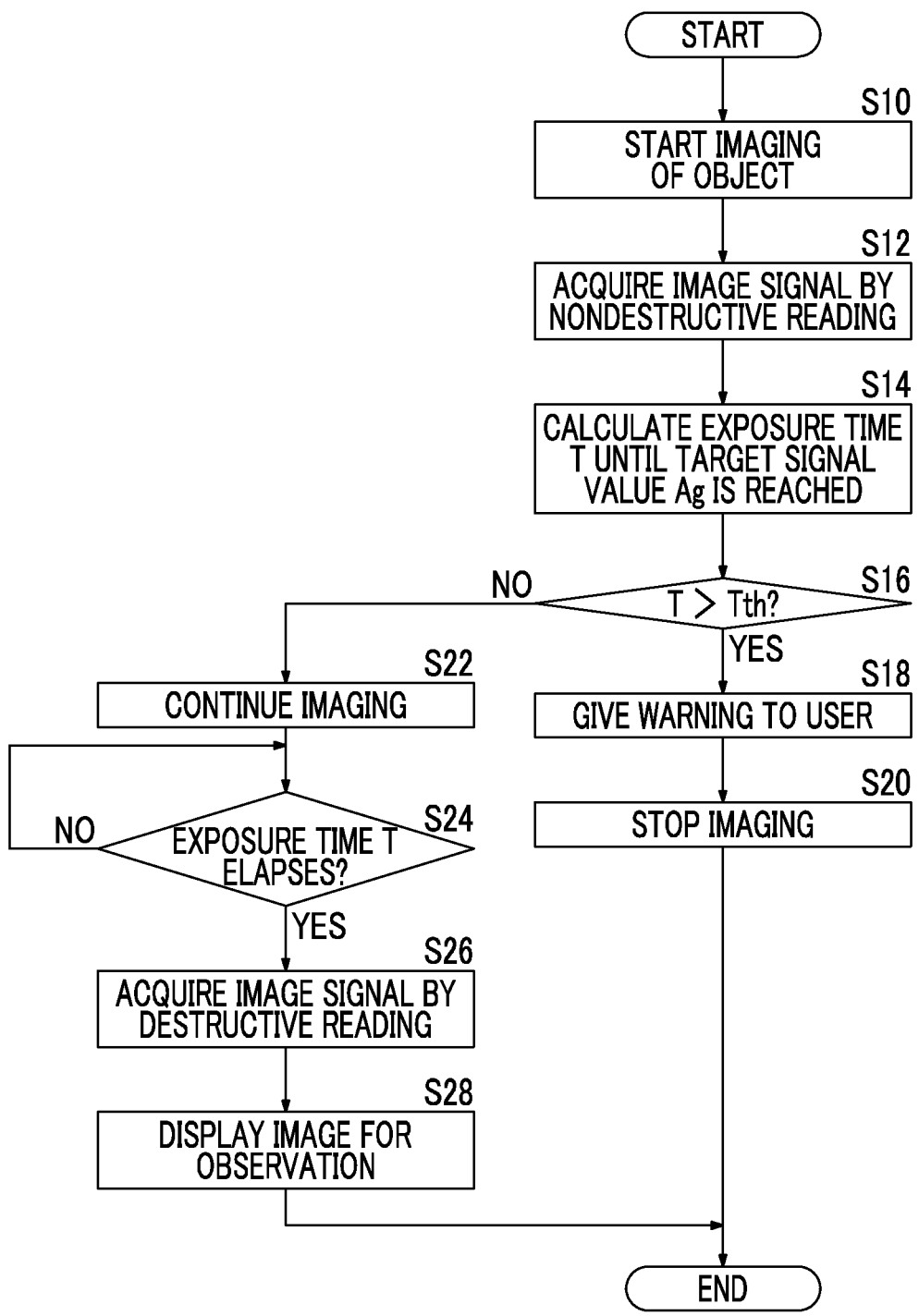
FIG. 4 is a flowchart illustrating the action of an imaging system using a first embodiment of an imaging device of the invention.

S30 to S40 shown in FIG. 7 are the same as S10 to S20 shown in FIG. 4. Then, in the flowchart shown in FIG. 7, even if it is determined in S36 that the exposure time T is equal to or less than the threshold value Th and imaging is continued (S42), in a case where the exposure time T does not elapse (S44, NO), nondestructive reading is performed again to acquire an image signal when the time set in advance has elapsed. Then, the exposure time T is calculated based on this image signal and the image signal acquired by previous nondestructive reading (S34), and the exposure time T is compared with the threshold value Tth.

Thereafter, the acquisition of the image signal by nondestructive reading, the calculation of the exposure time T based on this image signal and the image signal acquired by previous nondestructive reading, and the comparison of the exposure time T and the threshold value Tth are repeatedly performed until the exposure time T elapses. The timing when nondestructive reading is performed may be, for example, every second, but may be arbitrarily set by the user using the input unit 104.

In this way, the exposure time T is calculated each time the image signal is acquired by nondestructive reading, whereby it is possible to calculate the exposure time T with higher accuracy. S46 and S48 in FIG. 7 are the same as S26 and S28 shown in FIG. 4.

In the foregoing embodiment, although each time nondestructive reading is performed, the exposure time T is calculated based on this image signal and the image signal acquired by previous nondestructive reading, the image signal acquired by previous nondestructive reading may not necessarily be used, and each time nondestructive reading is performed, the exposure time T may be calculated using the image signal obtained by this single reading.

As in the foregoing embodiment, in a case where an image signal is acquired by nondestructive reading, the display control unit 115 may make the display unit 106 display an image for confirmation based on the image signal acquired by nondestructive reading. In this way, in a case where the image for confirmation is displayed, the user can confirm failure of sample creation visually. In a case where nondestructive reading is performed multiple times, it is preferable to sequentially display the image for confirmation each time the image signal of nondestructive reading is acquired.

Figure 8:
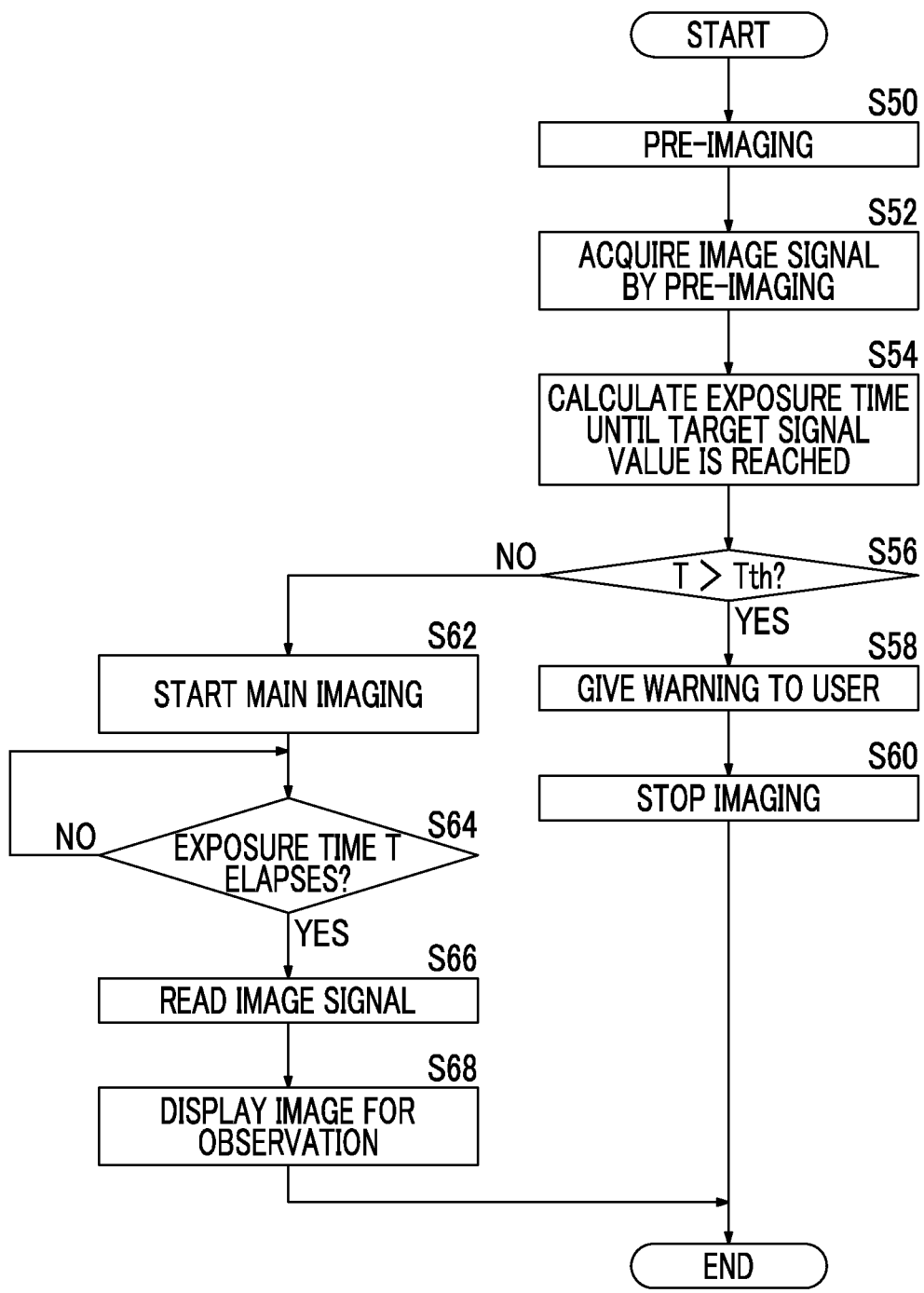
FIG. 8 is a flowchart illustrating the action of an imaging system using a second embodiment of an imaging device of the invention.

Next, an imaging system using a second embodiment of an imaging device and method of the invention will be described. In the imaging system of the first embodiment described above, although the exposure time is calculated based on the image signal acquired by nondestructive reading, the imaging system of the second embodiment is different from the imaging system of the first embodiment in that pre-imaging is performed before the start of imaging of main imaging for imaging the image for observation, and the exposure time is calculated based on the image signal acquired by pre-imaging. Hereinafter, description will be provided referring to the flowchart shown in FIG. 8 focusing on the difference from the imaging system of the first embodiment. In the imaging system of the second embodiment, since nondestructive reading described above is not performed, as the imaging element, a CCD image sensor, instead of a CMOS image sensor, may be used.

First, after the object S is placed on the stage 16 of the black box 10, a pre-imaging start instruction is input by the user using the input unit 104, and pre-imaging by the imaging unit 20 is started (S50).

Then, when a time t0 set in advance from the start of pre-imaging has elapsed, an image signal is read from the imaging element of the imaging unit 20 by destructive reading, and the image signal is acquired by the exposure time calculation unit 110 (S52).

Next, the exposure time calculation unit 110 calculates, based on the image signal acquired by pre-imaging, the exposure time until the signal value of the image signal reaches a target signal value set in advance (S54). A calculation method of the exposure time in this case is the same as the example shown in FIG. 5, and in a case where the signal value of the image signal acquired by pre-imaging is A0, the exposure time is calculated by $T=Ag/(A0/t0)$.

Then, the exposure time T calculated by the exposure time calculation unit 110 is output to the determination unit 112, and the determination unit 112 compares the input exposure time T with a threshold value Tth set in advance. In this case, instead of the threshold value determination of the exposure time T, threshold value determination of an exposure time obtained by subtracting the time t1 from the exposure time T, that is, a remaining exposure time, may be performed.

Then, in a case where the exposure time T exceeds the threshold value Tth (S56, YES), the determination unit 112 outputs a signal to that effect to the display control unit 115.

In a case where the signal to the effect that the exposure time T exceeds the threshold value Tth is input, as in the first embodiment, the display control unit 115 makes the display unit 106 display a message to the effect that creation of a sample fails, a message that a sample is abnormal, or the like, and gives a warning to the user (S58).

In a case where the signal to the effect that the exposure time T exceeds the threshold value Tth is input, the control unit 114 automatically stops the imaging operation of the imaging unit 20 (S60).

In a case where it is determined in the determination unit 112 that the exposure time T is equal to or less than the threshold value Tth (S56, NO), main imaging by the imaging unit 20 is started (S62). The start of main imaging may be automatically performed, or the user may instruct the start of main imaging again.

Then, after main imaging is started, when the exposure time T calculated by pre-imaging has elapsed (S64), the image signal is read from the imaging element of the imaging unit 20 by destructive reading and input to the image processing unit 108 (S66).

Then, after the image signal is subjected to the signal processes in the image processing unit 108, the image for observation is displayed on the display unit 106 based on the image signal subjected to the signal processes by the display control unit 115 (S68).

As in the second embodiment, in a case where the image signal is acquired by the pre-imaging, the display control unit 115 may make the display unit 106 display an image for confirmation based on the image signal acquired by the pre-imaging. In this way, in a case where the image for confirmation is displayed, the user can confirm failure of sample creation visually.

In the first and second embodiments, when the threshold value determination is performed in the determination unit 112, the threshold value Tth may be changed between in a case where an image of chemiluminescence of the object S is imaged and in a case where an image of fluorescence of the object S is imaged. This is because, for imaging an image of fluorescence, excitation light is reflected from the support or the like, a signal value of an image signal of a background by reflected light is great, and even if there is no fluorescence, the imaging element is likely to be saturated. In this way, since there is no meaning in the exposure by the time when the background is saturated, the threshold value may be reduced compared to a case of chemiluminescence not affected by the background described above. With this, it is possible to detect failure of sample creation with high accuracy.

In the first and second embodiments described above, for calculating the exposure time, although the linear function f or g is used, the invention is not limited to the linear function, and approximation may be made using a quadratic function, a higher-order function, or an exponential function.

In general, when comparing fluorescence and chemiluminescence, it is known that, in chemiluminescence, fading of a reagent is fast. Accordingly, an approximate expression for use in calculating the exposure time may be changed between in a case where an image of fluorescence is imaged and in a case where an image of chemiluminescence is imaged. For example, in a case where an image of fluorescence is imaged, the linear function may be used as the approximate expression, and in a case where an image of chemiluminescence is imaged, an exponential function or a function changes as an exponential function may be used. It is assumed that the linear function, the exponential function, or the function changing as an exponential function described above may be set in the exposure time calculation unit 110 in advance. However, the user may arbitrarily set the function using the input unit 104. Different functions may be set for the types of objects or the types of reagents.

In the first and second embodiments described above, for calculating the exposure time, it is desirable to increase sensitivity of the imaging element. Accordingly, for reading the image signal for use to calculate the exposure time, that is, for performing nondestructive reading of destructive reading of pre-imaging, binning reading may be performed. Binning reading is a method which collectively reads adjacent photoelectric conversion elements (pixels) in the imaging element. For example, if noise of one photoelectric conversion element is N, an ideal signal value with no noise read from one photoelectric conversion element is $a1$, and a target signal value of one photoelectric conversion element is $ag$, in a case where binning reading is not performed, the exposure time T becomes $T=ag/\{(a1+N)/t1\}$. Meanwhile, it is assumed that binning reading of four pixels is performed, and comparison of the accuracy of the exposure time is performed. In all of the four pixels for use in binning, it is assumed that an ideal signal value is $a1$, and noise is only a white noise component. In this case, the exposure time T becomes $T=4ag/\{(4a1+2N)/t1\}=ag/\{(a1+N/2)/t1\}$, and the influence of noise on the exposure time T becomes half. That is, it is possible to calculate the exposure time T with higher accuracy.

What is claimed is:

1. An imaging device comprising:
    an imaging unit which images an object;
    an exposure time calculation unit which calculates, based on an image signal acquired by imaging the object by imaging unit, an exposure time of the imaging until a signal value of the image signal reaches a target signal value set in advance;
    a determination unit which determines whether or not the exposure time exceeds a threshold value set in advance; and
    a notification unit which, in a case where it is determined that the exposure time exceeds the threshold value, gives notification of the result of the determination,
    wherein the imaging unit stops the imaging in a case where it is determined that the exposure time exceeds the threshold value, and
    wherein the determination unit changes the threshold value between in a case where chemiluminescence of the object is imaged and in a case where fluorescence of the object is imaged.

2. The imaging device according to claim 1,
    wherein the imaging unit has an imaging element which is able to read the image signal nondestructively, and
    the exposure time calculation unit calculates the exposure time based on the image signal read nondestructively.

3. The imaging device according to claim 2,
    wherein the exposure time calculation unit acquires image signal read multiple times nondestructively and continuously and calculates the exposure time based on the image signals acquired by reading multiple times.

4. The imaging device according to claim 3,
    wherein the exposure time calculation unit sequentially calculates the exposure time each time the image signal read nondestructively is acquired.

5. The imaging device according to claim 4, further comprising:
    a display control unit which makes a display unit sequentially display images based on the image signals read nondestructively and continuously.

6. The imaging device according to claim 3, further comprising:
    a display control unit which makes a display unit sequentially display images based on the image signals read nondestructively and continuously.

7. The imaging device according to claim 2,
    wherein the exposure time calculation unit sequentially calculates the exposure time each time the image signal read nondestructively is acquired.

8. The imaging device according to claim 7, further comprising:
    a display control unit which makes a display unit sequentially display images based on the image signals read nondestructively and continuously.

9. The imaging device according to claim 2, further comprising:
    a display control unit which makes a display unit sequentially display images based on the image signals read nondestructively and continuously.

10. The imaging device according to claim 1,
    wherein the imaging unit performs pre-imaging before main imaging, and
    the exposure time calculation unit calculates the exposure time based on an image signal acquired by the pre-imaging.

11. The imaging device according to claim 1,
    wherein the exposure time calculation unit changes a calculation expression for use in calculating the exposure time between in a case where chemiluminescence of the object is imaged and in a case where fluorescence of the object is imaged.

12. The imaging device according to claim 1,
    wherein the exposure time calculation unit acquires an image signal read with binning by the imaging unit and calculates the exposure time based on the acquired image signal.

13. The imaging device according to claim 1,
    wherein the notification unit performs a warning in a case where it is determined that the exposure time exceeds the threshold value.

14. The imaging device according to claim 13,
    wherein the notification unit makes a display unit display a warning message in a case where it is determined that the exposure time exceeds the threshold value.

15. An imaging method using an imaging device comprising an imaging unit, an exposure time calculation unit, a determination unit, and a notification unit, the method comprising:
    imaging, by the imaging unit, an object to acquire an image signal;
    calculating, by the exposing time calculation unit and based on only the acquire image signal, an exposure time of the imaging until a signal value of the image signal reaches a target signal value set in advance;
    determining, by the determination unit, whether or not the exposure time exceeds a threshold value set in advance; and
    in a case where it is determined that the exposure time exceeds the threshold value, giving notification, by the notification unit, of a result of the determination, and stopping the imaging, by the imaging unit,
    wherein the determination unit changes the threshold value between in a case where chemiluminescence of the object is imaged and in a case where fluorescence of the object is imaged.

* * * * *